US011768206B2

(12) United States Patent
Winchester

(10) Patent No.: US 11,768,206 B2
(45) Date of Patent: *Sep. 26, 2023

(54) METHODS OF TREATING OR PREVENTING SERIOUS SYMPTOMS FROM COVID-19 INFECTION

(71) Applicant: Henry Winchester, Newtown Square, PA (US)

(72) Inventor: Henry Winchester, Newtown Square, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/913,840

(22) Filed: Jun. 26, 2020

(65) Prior Publication Data

US 2021/0293827 A1 Sep. 23, 2021

Related U.S. Application Data

(60) Provisional application No. 62/992,975, filed on Mar. 21, 2020, provisional application No. 63/022,618, filed on May 11, 2020.

(51) Int. Cl.
| | |
|---|---|
| *G01N 33/68* | (2006.01) |
| *G01N 33/577* | (2006.01) |
| *G01N 33/53* | (2006.01) |
| *G01N 33/58* | (2006.01) |
| *A61K 45/06* | (2006.01) |

(52) U.S. Cl.
CPC ......... *G01N 33/6869* (2013.01); *G01N 33/53* (2013.01); *G01N 33/577* (2013.01); *G01N 33/68* (2013.01); *A61K 45/06* (2013.01); *G01N 33/582* (2013.01); *G01N 2800/50* (2013.01); *G01N 2800/60* (2013.01)

(58) Field of Classification Search
None
See application file for complete search history.

(56) References Cited

U.S. PATENT DOCUMENTS

2007/0092911 A1* 4/2007 Buechler ............ G01N 33/6893
435/7.1

OTHER PUBLICATIONS

Waiker et al. (J Am Soc Nephrol. Jan. 2012; 23(1): 13-21) (Year: 2012).*
Mayeux (NeuroRx. Apr. 2004;1(2):182-8) (Year: 2004).*
CDC information about COVID-19 treatments (downloaded May 7, 2021 from https://www.cdc.gov/coronavirus/2019-ncov/symptoms-testing/testing.html) (Year: 2021).*
Erdemli (Acta Orthop Traumatol Turc. Mar. 2018;52(2):143-147) (Year: 2018).*
Harvard Health (downloaded on May 7, 2021 from https://www.health.harvard.edu/diseases-and-conditions/treatments-for-covid-19) (Year: 2021).*
Chen et al. (J Virol. (2021) 95:e00014-21) (Year: 2021).*
Liu et al., "The potential role of IL-6 in monitoring severe case of coronavirus disease 2019," medRxiv, posted Mar. 10, 2020(https://www.medrxiv.org/content/10.1101/2020.03.01.20029769v2.full.pdf+html) (Date Accessed Apr. 19, 2021).
"Agreement with STC Biologics for GMP Manufacturing of an anti-Interleukin-6-Receptor Monoclonal Antibody for Clinical Studies in Patients with COVID-19," Tiziana Life Sciences, Jun. 29, 2020, https://www.tizianalifesciences.com/news-item?s=2020-06-29-agreement-with-stc-biologics-for-gmp-manufacturing-of-an-anti-interleukin-6-receptor-monoclonal-antibody-for-clinical-studies-in-patients-with-covid-19, Press Release (Date Accessed Apr. 19, 2021).
Terpos et al., "Hematological findings and complications of COVID-19," Am J Hematol. 2020; 95: 834-847.
Fan, B.E. et al., "Hematologic parameters in patients with COVID-19 infection," Am J Hematol. 2020; 95: E131-E153.
Hendry, B.M. et al., "Hypothesis: Pentoxifylline is a potential cytokine modulator therapeutic in COVID-19 patients," Pharmacol Res Perspect. 2020; e00631, pp. 1-5.
Donlan, A.N. et al., "IL-13 Predicts the Need for Mechanical Ventilation in COVID-19 Patients," medRxiv, Jun. 20, 2020 (https://www.medrxiv.org/content/10.1101/2020.06.18.20134353v1) (Date Accessed Apr. 19, 2021).
St. Petersburg State University,"High ferritin levels may indicate severe COVID-19," EurekAlert! Apr. 22, 2020, https://www.eurekalert.org/pub_releases/2020-04/spsu-hfl042220.php (Date Accessed Apr. 19, 2021).
Gavin, K., "Drug That Calms 'Cytokine Storm' Associated with 45% Lower Risk of Dying among COVID-19 Patients on Ventilators," University of Michigan Health Lab, Jul. 13, 2020, https://labblog.uofmhealth.org/body-work/drug-calms-cytokine-storm-associated-45-lower-risk-of-dying-among-covid-19-patients-on (Date Accessed Apr. 19, 2021).
Avril, T., "Temple study helps predict which COVID-19 patients develop dangerous 'cytokine storm'," The Philadelphia Inquirer, Oct. 21, 2020, https://www.inquirer.com/health/coronavirus/covid19-cytokine-storm-anakinra-temple-university-hospital-20201021.html (Date Accessed Apr. 19, 2021).
Zizzo, G et al., "Imperfect storm: is interleukin-33 the Achilles heel of COVID-19?," The Lancet Viewpoint, Dec. 1, 2020, vol. 2, Issue 12, pp. E779-E790.
Linkhorn, T., "Common antidepressant may reduce deadly COVID-19 complications,"Medical Xpress, Feb. 19, 2021, https://medicalxpress.com/news/2021-02-common-antidepressant-deadly-covid-complications.html (Date Accessed Apr. 19, 2021).
Caricchio, R et al., "Preliminary predictive criteria COVID-19 cytokine storm," Ann Rheum Dis, 2020, 0: 1-8. doi: 10. 1136/annrheumdis-2020-218323.

(Continued)

*Primary Examiner* — Brian Gangle
*Assistant Examiner* — Andrea K McCollum
(74) *Attorney, Agent, or Firm* — Quarles & Brady LLP

(57) ABSTRACT

Provided herein are methods for reducing risk of severe symptoms and outcomes associated with Coronavirus Disease 2019 (COVID-19) and Severe Acute Respiratory Syndrome Coronavirus 2 (SARS-CoV-2) infection by measuring levels of interleukin 6 (IL-6), IL-8, IL-22, and serum ferritin in a subject. Also provided are methods for treating a subject exposed to or at elevated risk of expose to SARS-CoV-2 based on levels of IL-6, IL-8, IL-22, and ferritin in the serum of the subject.

6 Claims, 2 Drawing Sheets

(56) References Cited

OTHER PUBLICATIONS

Petric, D., "Cytokine Storm in COVID-19," ResearchGate, uploaded Apr. 6, 2020, https://researchgate.net/publication/340463773.
Deng, H-J et al., "Cytokine Biomarkers of COVID-19," medRxiv, posted Jun. 3, 2020, https://doi.org/10.1101/2020.05.31.20118315.
Ulhaq ZS, S GV, "Interleukin-6 as a Potential Biomarker of COVID-19 Progression," Med Mal Infect, 2020. https://doi.org/10.1016/j.medmal.2020.04.002.
Cao,P et al., "Elevated Serum Ferritin Level Effectively Discriminates Severity Illness and Predicts Prognosis of COVID-19 Patients," Research Square, posted Jun. 2, 2020, https://doi.org/10.21203/rs.3.rs-31914/v1.
Pfeiffer, C.M. et al., "Laboratory Methodologies for Indicators of Iron Status: Strengths, Limitations, and Analytical Challenges," Am J Clin Nutr 2017; 106(Suppl.): 1606S-14S.
Wang, W et al., "Serum Ferritin: Past, Present and Future," Biochim Biophys Acta. , Aug. 2010; 1800(8): 760-769.
Garcia-Casal, M.N. et al., "Performance and Comparability of Laboratory Methods for Measuring Ferritin Concentrations in Human Serum or Plasma: A Systematic Review and Meta-Analysis," PLOS One, May 3, 2018, 13(5), 24 pages.
CDC Laboratory Procedure Manual, Ferritin in Serum, Apr. 2008.
Parks, O.B. et al., "Interleukin-22 Signaling in the Regulation of Intestinal Health and Disease," Front. Cell Dev. Biol., 2016, 3:85, pp. 1-13.
Qin, C., "Dysregulaion of Immune Response in Patients with Coronavirus 2019 (COVID-19) in Wuhan, China," Clinical Infectious Diseases, 2020, pp. 1-7.
Cytokine Storm Package for COVID-19 Research, IsoPlexis 2019.
Yoshikawa, T., "Severe Acute Respiratory Syndrome (SARS) Coronavirus-Induced Lung Epithelial Cytokines Exacerbate SARS Pathogenesis by Modulating Intrinsic Functions of Monocyte-Derived Macrophages and Dendritic Cells," Journal of Virology, Apr. 2009, vol. 83, No. 7, pp. 3039-3048.
Wu, D. et al., "TH17 Response in Cytokine Storm of COVID-19: An Emerging Target of JAK2 Inhibitor Fedratinib," Journal of Microbiology, Immunology and Infection, 2020, https://doi.org/10.1016/j.jmii.2020.03.005.
Cao, X, "COVID-19: Immunopathology and its Implications for Therapy," Nature Reviews, May 2020, vol. 20, pp. 269-270.
Mehta et al., "COVID-19: Consider Cytokine Storm Syndromes and Immunisuppression," The Lancet, Mar. 28, 2020, vol. 395, pp. 1033-1034.
Cha, S., "South Korean Doctors Find Risk Factors for Severe COVID-19 Cases," Yahoo! News, Jun. 11, 2020, https://news.yahoo.com/south-korean-doctors-risk-factors-020529753.html.
Trinity College Dublin, "Vitamin D Determines Severity in COVID-19: Researchers Urge Government to Change Advice," SciTech Daily, May 13, 2020, https://scitechdaily.com/vitamin-d-determines-severity-in-covid-19-researchers-urge-government-to-change-advice/.
Shields, M. et al., "WHO Moves to Update COVID-19 Guidance After "Great News" in Drug Study," Reuters, Jun. 17, 2020, https://www.msn.com/en-us/news/world/who-moves-to-update-covid-19-guidance-after-great-news-in-drug-study/ar-BB15ASLT?li=BBnb7Kz&ocid=SK216DHP.
Interleukin-6 (IL-6) Human ELISA Testing, abacus dx, Apr. 21, 2020, updated May 25, 2020, https://www.abacusdx.com/biochemistry/covid-19-interleukin-6-il-6-human-elisa-testing/.
Conti et al. "Induction of pro-inflammatory cytokines (IL-1 and IL-6) and lung inflammation by Coronavirus-19 (COVI-19 or SARS-COV-2); anti-inflammatory strategies", J Biol Regul Homeost Agents, Mar. 14, 2020, pp. 327-331.
Ding, L. et al., "Generation of High-Affinity Fully Human Anti-Interleukin-8 Antibodies from its cDNA by Two-Hybrid Screening and Affinity Maturation in Yeast", Protein Science, 2010, 19, pp. 1957-1966.
Laird et al., "Vitamin D and Inflammation: Potential Implications for Severity of Covid-19", Ir Med J., May 11, 2020, vol. 113, No. 5, p. 81.
Chouman, K. et al., "Characterization of new anti-IL-6 antibodies revealed high potency candidates for intracellular cytokine detection and specific targeting of IL-6 receptor binding sites," European Cytokine Network, 2018, 29(2), pp. 59-72.
Mao, L. et al., "Neurologic Manifestations of Hospitalized Patients with Coronavirus Disease 2019 in Wuhan, China," JAMA Neurol. 2020, 77(6), pp. 683-690.
Reynolds, S et al., "Quantification of Cytokines Using BDTM Cytometric Bead Array on the BDTM FACSVerse System and Analysis in FCAP ArrayTM Software," BD Biosciences, Jan. 2012, pp. 1-12.
Skikne, B.S et al., "An evaluation of monoclonal antibodies for serum ferritin measurements," Am J Clin Nutr., 1984, 40(2), pp. 346-350.
Andersen, K.M. et al., "Long-term use of immunosuppressive medicines and in-hospital COVID-19 outcomes: a retrospective cohort study using data from the National COVID Cohort Collaborative," Lancet Rheumatol 2022, vol. 4: e33-41.
Garcia, N. et al., "Deferasirox on COVID-19: safety and efficacy of iron-chelating therapy. A multicentric, randomized, triple blinded study," PPCR Journal 2021, vol. 7, No. 4, p. 38-46.
Henderson, E.(rev.), "Regular statin use may reduce the risk of death and severity of COVID-19," published on-line Oct. 24, 2022, retrieved from the Internet on Oct. 28, 2022 <https://www.news-medical.net/news/20221024/Regular-statin-use-may-reduce-the-risk-of-death-and-severity-of-COVID-19.aspx>.
Neurath, M.F., "COVID-19: biologic and immunosuppressive therapy in gastroenterology and hepatology," Nature Reviews 2021, vol. 18, 705-715.

* cited by examiner

FIG. 1

|  | All patients (N=452) | Nonsevere (n=166) | Severe (n=286) | P |
|---|---|---|---|---|
| Characteristics |  |  |  |  |
| Age, median (IQR), range, y | 58 (47–67), 22–95 | 53 (41.25–62), 22–92 | 61 (51–69), 26–95 | <.001 |
| Sex |  |  |  | .242 |
| Male | 235 (52.0) | 80 (48.2) | 155 (54.2) |  |
| Female | 217 (48.0) | 86 (51.8) | 131 (45.8) |  |
| Smoking | 7 (1.5) | 4 (2.4) | 3 (1.0) | .267 |
| Signs and symptoms |  |  |  |  |
| Fever | 423 (92.6) | 152 (91.6) | 271 (94.8) | .232 |
| Dry cough | 152 (33.3) | 56 (33.7) | 96 (33.6) | 1.000 |
| Expectoration | 189 (41.4) | 68 (41.0) | 121 (42.3) | .843 |
| Hemoptysis | 12 (2.6) | 2 (1.2) | 10 (3.5) | .225 |
| Shortness of breath | 232 (50.8) | 65 (39.2) | 167 (58.4) | <.001 |
| Myalgia | 98 (21.4) | 32 (19.3) | 66 (23.1) | .407 |
| Confusion | 3 (0.7) | 0 (0.0) | 3 (1.0) | .301 |
| Headache | 52 (11.4) | 13 (7.8) | 39 (13.6) | .068 |
| Dizziness | 37 (8.1) | 9 (5.4) | 28 (9.8) | .112 |
| Fatigue | 212 (46.4) | 65 (39.2) | 147 (51.4) | .014 |
| Rhinorrhea | 8 (1.8) | 2 (1.2) | 6 (2.1) | .716 |
| Pharyngalgia | 22 (4.8) | 10 (6.0) | 12 (4.2) | .376 |
| Anorexia | 96 (21.0) | 30 (18.1) | 66 (23.1) | .234 |
| Nausea and vomiting | 42 (9.2) | 10 (6.0) | 32 (11.2) | .092 |
| Diarrhea | 122 (26.7) | 44 (26.5) | 78 (27.3) | .913 |
| Abdominal pain | 23 (5.0) | 4 (2.4) | 19 (6.6) | .073 |

Data are median (IQR), n (%), in which N is the total number of patients with available data.

P values comparing severe and nonsevere cases are derived from $\chi^2$ test, Fisher' exact test, or Mann-Whitney $U$ test.

Abbreviations: COVID-19, coronavirus 2019; IQR, interquartile range.

FIG. 2

| Laboratory Findings | Normal Range | All Patients (N = 452) | Nonsevere (n = 166) | Severe (n = 286) | P |
|---|---|---|---|---|---|
| Infection-related biomarkers | | | | | |
| Procalcitonin, ng/mL | 0.0–0.05 | 0.1 (0.0–0.2) | 0.05 (0.03–0.09) | 0.1 (0.0–0.2) | <.001 |
| Erythrocyte sedimentation rate, mm/h | 0.0–15.0 | 31.5 (17.0–58.0) | 28.0 (14.0–50.0) | 34.0 (19.0–60.0) | .123 |
| Serum ferritin, ng/mL | 15.0–150.0 | 662.4 (380.9–1311.9) | 523.7 (299.1–840.4) | 800.4 (452.9–1451.6) | <.001 |
| C-reactive protein, mg/L | 0.0–1.0 | 44.1 (15.5–93.5) | 33.2 (8.2–59.7) | 57.9 (20.9–103.2) | <.001 |
| Inflammatory cytokines | | | | | |
| Tumor necrosis factor-α, pg/mL | 0.0–8.1 | 8.6 (6.9–10.9) | 8.4 (6.9–10.4) | 8.7 (7.1–11.6) | 0.37 |
| Interleukin-1β, pg/mL | 0.0–5.0 | 5.0 (5.0–5.0) | 5.0 (5.0–5.0) | 5.0 (5.0–5.0) | .962 |
| Interleukin-2R, U/mL | 223.0–710.0 | 714.5 (514.5–1040.3) | 663.5 (473.3–862.8) | 757.0 (528.5–1136.3) | .001 |
| Interleukin-6, pg/mL | 0.0–7.0 | 21.0 (6.1–47.2) | 13.3 (3.9–41.1) | 25.2 (9.5–54.5) | <.001 |
| Interleukin-8, pg/mL | 0.0–62.0 | 16.7 (10.2–27.0) | 13.7 (8.9–21.0) | 18.4 (11.3–28.4) | <.001 |
| Interleukin-10, pg/mL | 0.0–9.1 | 5.4 (5.0–9.7) | 5.0 (5.0–7.0) | 6.6 (5.0–11.3) | <.001 |
| Immunoglobulins | | | | | |
| Immunoglobulin A, g/L | 0.82–4.53 | 2.21 (1.65–2.79) | 2.14 (1.66–2.71) | 2.26 (1.57–2.89) | .285 |
| Immunoglobulin G, g/L | 7.51–15.60 | 11.75 (9.70–13.60) | 11.85 (10.13–13.40) | 11.7 (9.53–13.8) | .551 |
| Immunoglobulin M, g/L | 0.46–3.04 | 0.95 (0.70–1.31) | 1.02 (0.77–1.37) | 0.90 (0.69–1.28) | .033 |
| Complement proteins | | | | | |
| C3, g/L | 0.65–1.39 | 0.88 (0.77–1.00) | 0.88 (0.77–1.00) | 0.89 (0.77–1.00) | 0.942 |
| C4, g/L | 0.16–0.38 | 0.26 (0.20–0.31) | 0.26 (0.20–0.31) | 0.26 (0.20–0.31) | .851 |

Data are median (IQR). $P$ values comparing severe and nonsevere cases are derived from $\chi^2$ test, Fisher' exact test, or Mann-Whitney $U$ test.

Abbreviations: COVID-19, coronavirus 2019; IQR, interquartile range

METHODS OF TREATING OR PREVENTING SERIOUS SYMPTOMS FROM COVID-19 INFECTION

CROSS-REFERENCE TO RELATED APPLICATIONS

This application claims priority to U.S. Provisional Application No. 62/992,975, filed Mar. 21, 2020, and U.S. Provisional Application No. 63/022,618, filed May 11, 2020, each of which are incorporated herein by reference in their entirety.

STATEMENT REGARDING FEDERALLY SPONSORED RESEARCH

Not applicable.

REFERENCE TO A SEQUENCE LISTING SUBMITTED VIA EFS-WEB

Not applicable.

BACKGROUND

Coronaviruses (CoV) constitute a large family of positive-stranded, enveloped RNA viruses that infect a broad range of mammalian and avian species. The viruses cause primarily respiratory and enteric diseases. In the last two decades, three new zoonotic CoVs have emerged to infect humans. The most recent to emerge, of Severe Acute Respiratory Syndrome Coronavirus 2 (SARS-CoV-2), continues to spread globally and raises many scientific and public health questions and challenges. Development of rapid and effective diagnostic strategies is a pressing need. In particular, a need exists for rapid and effective strategies for providing a prognosis for Coronavirus disease 2019 (COVID-19) caused by SARS-CoV-2 infection, including identifying the most vulnerable subjects at risk for the most severe symptoms and clinical outcomes.

SUMMARY OF THE INVENTION

In a first aspect, provided herein is a method for estimating risk of severe Coronavirus Disease 2019 (COVID-19) symptoms in a subject, comprising (i) obtaining a biofluid sample from a subject exposed to or at high risk of exposure to Severe Acute Respiratory Syndrome Coronavirus 2 (SARS-CoV-2); and (ii) quantifying expression levels of at least three of IL-6, IL-8, IL-22 and ferritin. The expression levels may be measured by quantifying mRNA expression levels of at least three of IL-6, IL-8, IL-22, and ferritin in the biofluid sample by contacting the mRNA or cDNA derived therefrom with a probe or primer pairs specific to each of IL-6, IL-8, IL-22, and ferritin under conditions suitable for amplification to obtain an expression profile or by quantifying protein levels of at least three of IL-6, IL-8, IL-22, and ferritin in the biofluid sample by contacting total protein extracted from the whole blood sample or the serum sample with antibodies specific to IL-6, IL-8, IL-22, and ferritin under conditions suitable for detection of antibody binding to obtain an expression profile, wherein either the antibodies specific to IL-6, IL-8, IL-22, and ferritin or the total protein extracted from the whole blood sample or the serum sample are arrayed on a solid substrate or arrayed in a three-dimensional matrix. An increase in IL-6, IL-8, and IL-22 expression and an increase or decrease in ferritin expression relative to a healthy subject not exposed to SARS-CoV-2 indicates the subject is at risk of severe COVID-19 symptoms. In some embodiments, the antibodies specific to IL-6, IL-8, IL-22, and ferritin include a fluorescent tag. In some embodiments, the probes specific to IL-6, IL-8, IL-22, and ferritin mRNA or cDNA include a fluorescent tag.

In some embodiments, the biofluid is selected from the group consisting of whole blood, a blood product, saliva, sweat, urine, semen, tears, and cerebrospinal fluid. In some embodiments, the biofluid sample is a whole blood sample. In some embodiments, the biofluid sample is a blood product selected from the group consisting of a red blood cell sample, a white blood cell sample, a plasma sample, or a serum sample. In some embodiments, the method includes quantifying protein levels of IL-6, IL-8, IL-22 and ferritin in a serum sample from the subject.

In a second aspect, provided herein is a method for treating severe Coronavirus Disease 2019 (COVID-19) in a subject or treating a subject at high risk for severe COVID-19, comprising (i) obtaining a whole blood sample from a subject exposed to or at high risk of exposure to Severe Acute Respiratory Syndrome Coronavirus 2 (SARS-CoV-2) and (ii) quantifying expression levels of at least three of IL-6, IL-8, IL-22 and ferritin. The expression levels may be measured by (a) quantifying mRNA expression levels of at least three of IL-6, IL-8, IL-22, and ferritin in the whole blood sample or a white blood cell sample separated therefrom by contacting the mRNA or cDNA derived therefrom with a probe or primer pairs specific to each of IL-6, IL-8, IL-22, and ferritin under conditions suitable for amplification to obtain an expression profile; or (b) quantifying protein levels of at least three of IL-6, IL-8, IL-22, and ferritin in the whole blood sample or a serum sample separated therefrom by contacting total protein extracted from the whole blood sample or the serum sample with antibodies specific to IL-6, IL-8, IL-22, and ferritin under conditions suitable for detection of antibody binding to obtain an expression profile, wherein either the antibodies specific to IL-6, IL-8, IL-22, and ferritin or the total protein extracted from the whole blood sample or the serum sample are arrayed on a solid substrate or arrayed in a three-dimensional matrix. An increase in IL-6, IL-8, and IL-22 expression and an increase or decrease in ferritin expression relative to a healthy subject not exposed to SARS-CoV-2 indicates the subject has severe COVID-19 or is at risk for severe COVID-19 and said subject is treated with a therapeutically effective amount of an anti-inflammatory drug, an anticoagulant, a thrombolytic, an immunosuppressive agent, a metal chelator, an iron supplement, or a nutraceutical formulation, whereby severe COVID-19 it treated in the subject.

In some embodiments of the second aspect, the nutraceutical formulation includes Vitamin D, Vitamin C, quercetin, zinc, flaxseed Omega 3, buckthorn Omega 7, krill oil omegas, green tea, olive leaf, garlic, apple, strawberry, papaya, spinach, broccoli, pea, turmeric, grape seed, pycnogenol, a probiotic, or combinations thereof. In some embodiments, the anti-inflammatory drug is a non-steroidal anti-inflammatory drug (NSAID), a glucocorticoid, or a statin. In some embodiments, the immunosuppressive agent is selected from the group consisting of anakinra, tocilizumab, baricitinib, ruxolitinib, and sarilumab. In some embodiments, the metal chelator is selected from the group consisting of deferasirox, deferiprone, and deferoxamine. In some embodiments, the iron supplement is selected from the group consisting of ferrous sulfate, ferrous gluconate, ferrous fumarate, ferumoxytol, iron sucrose, iron polysaccharide, iron dextran, heme iron polypeptide, carbonyl iron, ferric carboxymaltose, ferric citrate, ferric derisomaltose, and ferric maltol.

In a third aspect, provided herein is a method for reducing risk of severe COVID-19 symptoms in a subject, comprising (i) obtaining a whole blood sample from a subject exposed to or at high risk of exposure to SARS-CoV-2 and (ii) quantifying expression levels of at least three of IL-6, IL-8, IL-22 and ferritin. The expression levels are measured by (a) quantifying mRNA expression levels of at least three of IL-6, IL-8, IL-22, and ferritin in the whole blood sample or a white blood cell sample separated therefrom by contacting the mRNA or cDNA derived therefrom with a probe or primer pairs specific to each of IL-6, IL-8, IL-22, and ferritin under conditions suitable for amplification to obtain an expression profile; or (b) quantifying protein levels of at least three of IL-6, IL-8, IL-22, and ferritin in the whole blood sample or a serum sample separated therefrom by contacting total protein extracted from the whole blood sample or the serum sample with antibodies specific to IL-6, IL-8, IL-22, and ferritin under conditions suitable for detection of antibody binding to obtain an expression profile, wherein either the antibodies specific to IL-6, IL-8, IL-22, and ferritin or the total protein extracted from the whole blood sample or the serum sample are arrayed on a solid substrate or arrayed in a three-dimensional matrix. An increase in IL-6, IL-8, and IL-22 expression and an increase or decrease in ferritin expression relative to a healthy subject not exposed to SARS-CoV-2 indicates the subject has severe COVID-19 or is at risk for severe COVID-19 and said subject receives a therapeutically effective amount of an anti-inflammatory drug, an anticoagulant, a thrombolytic, an immunosuppressive agent, a metal chelator, an iron supplement, or a nutraceutical formulation, whereby the risk of severe COVID-19 symptoms in the subject is reduced.

In some embodiments of the third aspect, the nutraceutical formulation includes Vitamin D, Vitamin C, quercetin, zinc, flaxseed Omega 3, buckthorn Omega 7, krill oil omegas, green tea, olive leaf, garlic, apple, strawberry, papaya, spinach, broccoli, pea, turmeric, grape seed, pycnogenol, a probiotic, or combinations thereof. In some embodiments, the anti-inflammatory drug is a non-steroidal anti-inflammatory drug (NSAID), a glucocorticoid, or a statin. In some embodiments, the immunosuppressive agent is selected from the group consisting of anakinra, tocilizumab, baricitinib, ruxolitinib, and sarilumab. In some embodiments, the metal chelator is selected from the group consisting of deferasirox, deferiprone, and deferoxamine. In some embodiments, the iron supplement is selected from the group consisting of ferrous sulfate, ferrous gluconate, ferrous fumarate, ferumoxytol, iron sucrose, iron polysaccharide, iron dextran, heme iron polypeptide, carbonyl iron, ferric carboxymaltose, ferric citrate, ferric derisomaltose, and ferric maltol.

In a forth aspect, provided herein is a method for determining risk of severe COVID-19 symptoms in a subject comprising (i) obtaining a biofluid sample from a subject exposed to or at high risk of exposure to SARS-CoV-2 and (ii) measuring expression levels of at least three of IL-6, IL-8, IL-22, and ferritin in the biofluids sample, wherein an increase in IL-6, IL-8, and IL-22 expression and an increase or decrease in ferritin expression relative to a healthy subject not exposed to SARS-CoV-2 indicates that the subject is at risk for severe COVID-19 symptoms.

BRIEF DESCRIPTION OF DRAWINGS

FIG. 1 shows demographic and baseline characteristics of patients with COVID-19 as reported by Qin et al. ("Dysregulation of immune response in patients with Coronavirus 2019 (COVID-19) in Wuhan, China," Clinical Infectious Diseases, Mar. 12, 2020).

FIG. 2 shows laboratory findings of patients with COVID-19 as reported by Qin et al.

INCORPORATION BY REFERENCE

All publications, patents, and patent applications mentioned in this specification are herein incorporated by reference to the same extent as if each individual publication, patent, and patent application was specifically and individually indicated to be incorporated by reference.

DETAILED DESCRIPTION OF THE INVENTION

The present disclosure describes methods and assays for determining risk of severe symptoms associated with SARS-CoV-2 infection and COVID-19. In particular, the methods described herein help to identify the subjects at greatest risk for the most severe COVID-19 symptoms and clinical outcomes and to identify underlying risk factors in a subject that contribute to the severe clinical outcomes.

In general as described herein, a method for estimating risk of severe symptoms includes quantifying of cytokines interleukin 6 (IL-6), IL-22, and IL-8 in a biofluid sample from a subject exposed to or at high risk of exposure to Severe Acute Respiratory Syndrome Coronavirus 2 (SARS-CoV-2). The method for estimating risk may also include quantifying serum ferritin or measuring serum transferrin saturation. Methods for quantification of cytokines and other analytes in biofluids are known and described in the art. See, for example, Reynolds et al. ("Quantification of cytokines using BD™ cytometric bead array on the BD™ FACSVerse system and analysis in FCAP Arry™ software," BD Biosciences, January 2012). Unless otherwise indicated herein, assay methods described herein use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2nd edition).

The methods for estimating risk of severe symptoms consists of assaying levels of IL-6, IL-8, and IL-22 in a biofluid sample from a subject. The methods for estimating risk of severe symptoms may alternatively consist of assaying levels of at least 3 of IL-6, IL-8, IL-22, and ferritin. The methods for estimating risk of severe symptoms may alternatively consist of assaying levels of IL-6, IL-8, IL-22, and ferritin. The methods described here provide the benefit of assaying risk of severe COVID-19 by assaying IL-6, IL-8, IL-22, and ferritin alone.

Severe symptoms or severe outcomes from SARS-CoV-2 infection or COVID-19 may include, but are not limited to, cytokine storm, shortness of breath, low blood oxygen saturation, aggressive progression of pulmonary inflammation, low resting heart rate (bradycardia), acute respiratory distress, stroke, abnormal blood clotting, neurological manifestations, and death. The neurological manifestations may include, but are not limited to, effects on the central nervous system (e.g., dizziness, headache, impaired consciousness, acute cerebrovascular disease, ataxia, and seizure), peripheral nervous system (e.g., taste impairment, smell impairment, vision impairment, and nerve pain), and skeletal muscular injury. Use of the assay methods described here can identify subjects at particular risk for these symptoms or outcomes and measures can be taken, including one or more treatments as described herein, to prevent onset of the severe symptoms or outcomes.

As reported by Qin et al. ("Dysregulation of immune response in patients with Coronavirus 2019 (COVID-19) in Wuhan, China," Clinical Infectious Diseases, Mar. 12, 2020), patients with severe infections had respiratory distress with a respiratory rate over 30 breaths per minutes, an oxygen saturation ≤93% in the resting state, and an arterial blood oxygenation partial pressure ($PaO_2$)/oxygen concentration ($FiO_2$)≤300 mm Hg. Characteristics and symptoms for these patients are reported in FIG. 1, which was originally reported by Qin et al. FIG. 1 also shows the particular symptoms associated with severe COVID-19. In patients with severe infection, levels of IL-8 and IL-6 were significantly increased (P-value<0.001) compared to patients with non-severe infections. (FIG. 2) Likewise, serum ferritin was significantly increased (P-value<0.001) in patients with severe infections. (FIG. 2)

A subject exposed to SARS-CoV-2 is a subject who's had close personal contact with or who's been in the immediate proximity of someone infected with SARS-CoV-2. As used herein, a subject "at high risk of exposure to SARS-CoV-2" refers to a subject in frequent contact with members of the public, in frequent contact with patients diagnosed with COVID-19, or having a close relative or member of one's household who is in frequent contact with the public or patients diagnosed with COVID-19. For example, subjects at high risk of exposure to SARS-CoV-2 may include, but are not limited to, medical professionals, first responders, public works employees, grocery store employees, food service employees, pharmacy employees, those who operate or use public transportation, retail workers, the family or household members thereof, and the like.

As used herein, "biofluid" refers to a biological fluid produced by a subject. Suitable biofluids include, but are not limited to, blood, a blood product, saliva, sweat, urine, semen, tears, and cerebrospinal fluid. In some embodiments, the biofluid is selected from the group consisting of blood, saliva, sweat, urine, semen, tears, and cerebrospinal fluid. In some embodiments, the biofluid is blood or a blood product. In some embodiments, the biofluid is a blood product which is a fraction separated from a whole blood sample, for example, a red blood cell sample, a white blood cell sample, a plasma sample, or a serum sample. Methods for separating individual fractions from a whole blood sample are known and described in the art. For example, a white blood cell sample may be separated from a whole blood sample using leukapheresis.

In some embodiments, the biofluid sample is from a subject previously diagnosed with rheumatoid arthritis, Crohn's disease, chronic obstructive pulmonary disease (COPD), psoriasis, cardiovascular disease, periodontitis, Tuberculosis (TB), asthma, sinusitis, atopic dermatitis, ulcerative colitis, peptic ulcer, systemic lupus, inflammatory bowel disease, atherosclerosis, scleroderma, multiple sclerosis, Alzheimer's, chronic inflammation irritable bowel syndrome, leaky gut, gout, or Lyme disease.

In some embodiments, expression level of a cytokine or analyte is based on quantification of protein or peptides in the biofluid sample. Suitable methods for protein, peptide, and antibody quantification in a sample are known in the art and may include, but are not limited to, enzyme-linked immunosorbent assay (ELISA), Western blot, immunoassay (e.g., immunofluorescence assay), and mass spectrometry. In general, the level of a protein or peptide present in a sample may be quantified by contacting the sample with an antibody specific to the protein or peptide of interest. The antibody specific to the protein or peptide of interest may be labeled with one or more fluorescent labels for direct detection and quantification of the protein or peptide of interest. In some embodiments, the detection and quantification of the primary antibody bound to the target protein or peptide is achieved through a second labeled detection antibody specific to the primary antibody bound to the protein or peptide of interest. In some embodiments, the antibody specific to the protein or peptide of interest is arrayed on a substrate.

In some embodiments, proteins or peptides from the biofluid sample are arrayed on or within a three-dimensional matrix for detection and quantification. For example, the peptides or proteins from the biofluid sample can be run on a gel and the gel may be contacted with antibodies specific to the protein or peptides of interest.

For quantification, detection, or separation, the antibodies specific to the protein or peptide of intersect may be labeled. The label may be a fluorescent tag, a small molecule, a macromolecule, or an enzyme. In some embodiments, the antibody is labeled with a fluorescent tag for fluorescent detection, quantification, and/or separation of the protein or peptide of interest. Suitable fluorescent tags are known and described in the art and may include, but are not limited to, green fluorescent protein (GFP), yellow fluorescent protein (YFP), mCherry, dsRed, and the like. In some embodiments, the antibody is labeled with a small molecule or macromolecule tag for detection, quantification, and/or separation of the protein or peptide of interest. Suitable small molecule and macromolecular tags are known and described in the art and may include, but are not limited to, biotin, streptavidin, a poly-histidine tag, c-Myc, a FLAG® tag (an eight amino acid peptide tag that is hydrophobic and contains an enterokinase cleavage site), and the link. In some embodiments, the antibody is labeled with an enzyme for detection, quantification, and/or separation of the protein or peptide of interest. Suitable reporter enzymes are known and described in the art and may include, but are not limited to, horseradish peroxidase (HRP), alkaline phosphatase (ALP), glucose oxidase (GO) and beta galactosidase (BGAL or ßgal).

In some embodiments, expression levels of a cytokine or other analyte is based on quantification of mRNA present in the biofluids sample. Suitable methods for mRNA quantification are known in the art and may include, but are not limited to, polymerase chain reaction (PCR), quantitative PCR (qPCR), reverse transcription PCR (RT-PCR, whereby cDNA derived from the mRNA is quantified), real time PCR, Northern blot, nuclease protection assay, and in situ hybridization. In general, the level of mRNA, or cDNA derived therefrom, may be quantified by contacting the sample, or mRNA extracted from the sample, with a probe or primer pair specific to the mRNA of interest for quantification. The primer pair is designed to amplify the entirety or a portion of the cytokine or analyte mRNA or cDNA of interest. In general, the primer pair is between about 5 base pairs (bp) and about 80 bp, about 10 bp to about 65 bp, about 15 bp to about 50 bp, or about 18 bp to about 40 bp in length. Methods for primer design are known and described in the art. Those of skill in the art understand the degeneracy of the genetic code and that a variety of polynucleotide primers specific to the mRNA and cDNA of interest can be designed and used to yield similar results.

In some embodiments, the methods to quantify the level of a cytokine or other analyte using mRNA or cDNA may include one or more labeled probes or primers for quantification. Similar to the primer pairs a probe specific to the mRNA or cDNA of interest may be between about 5 base pairs (bp) and about 80 bp, about 10 bp to about 65 bp, about 15 bp to about 50 bp, or about 18 bp to about 40 bp in length. Likewise, suitable labels are known in the art and may include, but are not limited to, fluorescent labels.

In some embodiments, the level of interleukin 6 (IL-6) in a biofluid sample is measured as an indicator of risk. IL-6 is a pro-inflammatory cytokine with anti-inflammatory properties. IL-6 signaling may be mediated by the membrane bound IL-6 receptor (IL-6R) to initiate signaling via the JAK-STAT and MAPK pathways (i.e., classical IL-6 signaling) or through soluble IL-6R (sIL-6R) to induce gp130 signaling (i.e., trans IL-6 signaling). These IL-6 signaling pathways play an essential role in the immune response to viral infections, such as SARS-CoV-2, and may be considered an early warning signal for a viral infection. High expression and cellular levels of IL-6 may be an indicator of chronic inflammation and auto-immunity and regulation of IL-6 has a potential to impact cytokine release syndrome (i.e., cytokine storm). IL-6 may be used as an indicator of disruptions or complications with in the cardio-pulmonary system, for example, as an indicator of asthma. IL-6 is also an indicator of arthritis.

In some embodiments, a biofluid sample may be contacted with an antibody specific to IL-6. Antibodies specific to IL-6 are known and described in the art. Suitable IL-6 antibodies include, but are not limited to, MAB206, MQ2-13A5, MQ2-39C3, B-E8, MAB227, and AT1H6. See, for example, Chouman et al. ("Characterization of new anti-IL-6 antibodies revealed high potency candidates for intracellular cytokine detection and specific targeting of IL-6 receptor binding sites," European Cytokine Network, 2018, 29, 59-72). In some embodiments, a biofluid sample may be contacted with a probe or primer pair specific to IL-6 mRNA or a cDNA derived therefrom.

In some embodiments, the level of interleukin 22 (IL-22) in a biofluid sample is measured as an indicator of risk. IL-22 is a member of the IL-10 superfamily of cytokines and plays a role in a wide range of immune functions. IL-22 is an indicator of disruptions or complications within the gastrointestinal (GI) system, for example, as an indicator of inflammatory bowel disease (IBD). Expression levels of IL-22 provide insight on Natural Kill cells, T cells, and innate lymphoid cells. Additionally, the role of IL-22 in pathogen defense has been identified in the upper GI track, the oral cavity, salivary glands, tonsils, esophagus, and stomach. IL-22 also plays a role in rheumatoid arthritis by inducing proliferation and chemokine production in fibroblasts.

In some embodiments, a biofluid sample may be contacted with an antibody specific to IL-22. Antibodies specific to IL-22 are known and described in the art. Suitable IL-22 antibodies include, but are not limited to, IL22JOP, 22URTI, 1H8PWSR, MAB7822, and AF782. In some embodiments, a biofluid sample may be contacted with a probe or primer pair specific to IL-22 mRNA or a cDNA derived therefrom.

In some embodiments, the level of interleukin 8 (IL-8) in a biofluid sample is measured as an indicator of risk. IL-8, also known in the art as chemokine C-X-C motif ligand 8 (CXCL8), is a cytokine produced by a variety of tissues and cell types. IL-8 is upregulated by oxidative stress and itself plays a role in the large release of reactive oxygen species (ROS) from neutrophils known as "respiratory burst." IL-8 is active in the immune response from neutrophils and granulocytes, for example, in response to viral or bacterial infection. IL-8 can likewise be an indicator of neutrophil or granulocyte overstimulation as an early indication of cytokine release syndrome or cytokine storm. IL-8 expression is also connected to obesity, gingivitis, and psoriasis. Bronchiolitis, a common respiratory tract disease caused by viral infection is also linked to an increase in IL-8 expression.

In some embodiments, a biofluid sample may be contacted with an antibody specific to IL-8. Antibodies specific to IL-8 are known and described in the art. Suitable IL-8 antibodies include, but are not limited to, CI0925, MAB208, 8M6 (MAB1044), E8N1, and 3IL8-H10. See, for example, Ding et al. ("Generation of high-affinity fully human anti-interleukin-8 antibodies from its cDNA by two-hybrid screening and affinity maturation in yeast," Protein Sci., 2010, 19(10):1957-1966). In some embodiments, a biofluid sample may be contacted with a probe or primer pair specific to IL-8 mRNA or a cDNA derived therefrom.

In some embodiments, the method additionally includes quantifying ferritin protein levels in a serum sample from the subject. Methods for quantification of ferritin are known and described in the art. See, for example, Garcia-Casal et al. (Performance and comparability of laboratory methods for measuring ferritin concentration in human serum or plasm: A systematic review and meta-analysis," PLoS One, 2018, 13(5):e0196576), Sampson ("CDC Laboratory Procedure Manual, Ferritin Serum, April 2008), and Wang et al. ("Serum Ferritin: Past, Present, and Future," Biochim. Biophys. Acta., 2010, 1800(8):760-769). In some embodiments, ferritin may be quantified by contacting the biofluid sample with an antibody specific to ferritin. Suitable ferritin antibodies are known and described in the art and may include, but are not limited to, MAB93541, EPR3004Y, and F5012. Also see, Skikne et al. ("An evaluation of monoclonal antibodies for serum ferritin measurements," Am. J. Clin. Nutr., 1984, 40(2):346-350).

In some embodiments, the method additionally includes measuring serum transferrin saturation. Suitable methods are known and described in the art for measuring serum transferrin saturation. See, for example, Pfeiffer et al. ("Laboratory methodologies for indicators of iron status: strengths, limitations, and analytical challenges," Am. J. Clin. Nutr., 2017, 106 (Suppl 6):1606S-1614S).

As used herein, the terms "treat" and "treating" refers to therapeutic measures, wherein the object is to slow down (lessen) an undesired physiological change or pathological disorder resulting from COVID-19 or SARS-CoV-2 infection as described herein. For purposes of this invention, treating the disease includes, without limitation, alleviating one or more clinical symptoms, decreasing inflammation, reducing the severity of one or more clinical symptoms of the disease or injury, diminishing the extent of the condition, stabilizing the subject's disease or injury (i.e., not worsening), delay or slowing, halting, or reversing the disease and bringing about partial or complete remission of the disease. Treating the disease also includes prolonging survival by days, weeks, months, or years as compared to prognosis if treated according to standard medical practice not incorporating testing and subsequent treatment as described herein.

Subjects in need of treatment can include those whom, based on the testing methods described herein, are at increased risk for severe symptoms or outcomes associated with COVID-19 or SARS-CoV-2 infection. Pre-treating or preventing COVID-19 according to a method of the present invention includes initiating the administration of a therapeutic at a time prior to the appearance or existence of COVID-19 symptoms, based on the outcomes of the tests described herein. Pre-treating COVID-19 is particularly applicable to subjects at risk of having or acquiring severe symptoms or clinical outcomes as determined by the testing methods described herein. As used herein, the terms "prevent" and "preventing" refer to prophylactic or preventive measures intended to inhibit undesirable physiological changes or the development of severe symptoms resulting from COVID-19. In exemplary embodiments, preventing severe COVID-19 symptoms comprises initiating the administration of a therapeutic at a time prior to the appearance or existence of severe COVID-19 symptoms such that COVID-19, or in particular its severe symptoms, pathological features, consequences, or adverse effects do not occur. In such cases, a method of the invention for preventing severe COVID-19 symptoms and outcomes comprises administering a therapeutic to a subject in need thereof prior to the onset of symptoms and based on the results of the tests described herein.

As used herein, the terms "subject" or "patient" are used interchangeably and can encompass any human, regardless of age or gender. As used herein, the phrase "in need thereof" indicates the state of the subject, wherein therapeutic or preventative measures are desirable. In particular, a subject in need of treatment is a subject with increased risk of severe COVID-19 related symptoms based on the tests described herein. A subject in need of treatment is a subject with increased levels of IL-6, IL-8, and IL-22. In some embodiments, a subject in need of treatment is a subject with increased levels of IL-6, IL-8, and IL-22 and increased or decreased levels of serum ferritin.

In some aspects, provided herein is a method for treating a subject with high risk for severe COVID19 symptoms as determined by the assays described herein. After a subject is determined to be at high risk for severe symptoms, the subject may receive an effective amount of an anti-inflammatory drug, an anticoagulant, a thrombolytic, an immunosuppressive agent, a metal chelator, an iron supplement, or a nutraceutical formulation to treat or prevent the severe COVID19 symptoms.

In some embodiments, the nutraceutical formulation includes Vitamin D, Vitamin C, quercetin, zinc, flaxseed Omega 3, buckthorn Omega 7, krill oil omegas, green tea, olive leaf, garlic, apple, strawberry, papaya, spinach, broccoli, pea, turmeric, grape seed, PYCNOGENOL® (extract of French maritime pine bark (*Pinus pinaster*)), a probiotic, a probiotic blend, or combinations thereof.

In some embodiments, the anti-inflammatory drug is a non-steroidal anti-inflammatory drug (NSAID) or a glucocorticoid. In some embodiments, the anti-inflammatory drug is a statin and is administered to reduce C-reactive proteins and lower low-density lipoprotein (LDL). In some embodiments, the anti-inflammatory drug is colchicine. In some embodiments, the anti-inflammatory drug is pentoxifylline.

In some embodiments, the immunosuppressive agent is selected from the group consisting of anakinra, tocilizumab, baricitinib, ruxolitinib, and sarilumab, In some embodiments, the metal chelator is selected from the group consisting of deferasirox, deferiprone, and deferoxamine. In some embodiments, the iron supplement is selected from the group consisting of ferrous sulfate, ferrous gluconate, ferrous fumarate, ferumoxytol, iron sucrose, iron polysaccharide, iron dextran, heme iron polypeptide, carbonyl iron, ferric carboxymaltose, ferric citrate, ferric derisomaltose, and ferric maltol.

Therapeutically effective amounts of an anti-inflammatory drug, an anticoagulant, a thrombolytic, an immunosuppressive agent, a metal chelator, an iron supplement, or a nutraceutical formulation are administered to a subject in need thereof. An effective dose or amount is an amount sufficient to effect a beneficial or desired clinical result. With regard to methods of the present invention, the effective dose or amount, which can be administered in one or more administrations, is the amount of an anti-inflammatory drug, an anticoagulant, a thrombolytic, an immunosuppressive agent, a metal chelator, an iron supplement, or a nutraceutical formulation sufficient to elicit a therapeutic effect in a subject to whom it is administered. Effective amounts will be affected by various factors that modify the action of the therapeutic upon administration and the subject's biological response to the therapeutic, e.g., severity of COVID-19 symptoms, extent and severity of inflammation, the subject's age, sex, and diet, time of administration, and other clinical factors.

Therapeutically effective amounts for administration to a human subject can be determined in animal tests and any art-accepted methods for scaling an amount determined to be effective for an animal for human administration. For example, an amount can be initially measured to be effective in an animal model (e.g., to achieve a beneficial or desired clinical result). The amount obtained from the animal model can be used in formulating an effective amount for humans by using conversion factors known in the art. The effective amount obtained in one animal model can also be converted for another animal by using suitable conversion factors such as, for example, body surface area factors.

It is to be understood that, for any particular subject, specific dosage regimes should be adjusted over time according to the individual need and the professional judgment of the person administering or supervising the administration of the washed equine platelet extract. For example, dosage of the therapeutic for a particular subject with severe inflammation associated with COVID-19 can be increased if the lower dose does not elicit a detectable or sufficient improvement in inflammation. Conversely, the dosage can be decreased if the inflammation is treated or eliminated.

In some cases, therapeutically effective amounts of the therapeutic can be determined by, for example, measuring the effects of a therapeutic in a subject by incrementally increasing the dosage until the desired symptomatic relief level is achieved. A continuing or repeated dose regimen can also be used to achieve or maintain the desired result. Any other techniques known in the art can be used as well in determining the effective amount range. Of course, the specific effective amount will vary with such factors as the particular disease state being treated, the physical condition of the subject, the duration of the treatment, route of administration, and the nature of any concurrent therapy.

Following administration of the therapeutic to an individual subject likely to develop severe symptoms associated with COVID-19, a clinical symptom or feature associated with COVDI-19 is observed and assessed for a positive or negative change. For example, for methods of treating cytokine storm in a subject, positive or negative changes in the subject's levels of 11-6, IL-8, and 11-22 during or following treatment may be determined as described herein or by any means known in the art. The subject's levels of IL-6, IL-8, and IL-22 may continue to be monitored and treatment altered to improve on or reduce severe COVID-19 symptoms and clinical outcomes. Likewise, the subject's level of serum ferritin or transferrin saturation may be monitored and treatment modified based on the results.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of." "Consisting essentially of," when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

The present invention has been described in terms of one or more preferred embodiments, and it should be appreciated that many equivalents, alternatives, variations, and modifications, aside from those expressly stated, are possible and within the scope of the invention.

Prophetic Example 1

The embodiments described in this prophetic example demonstrate the correlation between levels of IL-6, IL-8, IL-22, and ferritin in a biofluid sample from a subject and severe clinical COVID-19 symptoms in the subject. In general, the subject is a subject diagnosed with COVID-19 as indicated by an infection with SARS-CoV-2. The severity of COVID-19 is analyzed based on the subjects presentation with the symptoms described herein. For example, severity of COVID-19 may be assessed or analyzed based on the subject's level of respiratory distress, the subject's blood oxygen saturation, the subject's blood oxygen pressure/oxygen concentration level ($PaO_2/FiO_2$), the subjects' resting heart rate, and/or manifestation of one or more neurological symptoms in the subject. The severity of COVID-19 may be quantified by adding a score or qualifier to one or more of the symptoms described.

Subjects in the study may be retrospectively recruited. For example, clinical data from subjects may be extracted from electronic medical records as part of a retrospective study. In general, any data that records the severity of COVID-19 in the subject (i.e., as indicated by the symptoms described above) as well as the levels of IL-6, IL-8, IL_22, and ferritin as measured in a whole blood, platelet, or serum sample from the subject are suitable for use in this study. Correlation between (i) each of IL-6, IL-8, IL-22, and ferritin and (ii) severity of COVID-19 will be calculated. Additionally, a model may be fit to predict COVID-19 severity based on blood, serum, or plasma levels of IL-6, IL-8, IL-22, and ferritin.

I claim:

1. A method for treating or preventing severe Coronavirus Disease 2019 (COVID-19) symptoms in a subject exposed to or infected with Severe Acute Respiratory Syndrome Coronavirus 2 (SARS-CoV-2), the method consisting of:
   (i) obtaining a whole blood sample from the subject;
   (ii) quantifying protein levels of at least three of interleukin 6 (IL-6), IL-8, IL-22, and ferritin in the whole blood sample or a serum sample separated therefrom by contacting total protein extracted from the whole blood sample or the serum sample with antibodies specific to IL-6, IL-8, IL-22, and ferritin under conditions suitable for detection of antibody binding to obtain an expression profile, wherein either the antibodies specific to IL-6, IL-8, IL-22, and ferritin or the total protein extracted from the whole blood sample or the serum sample are arrayed on a solid substrate or arrayed in a three-dimensional matrix;
   (iii) determining that the subject compared to a healthy subject has at least three of (1) an increase in IL-6, (2) an increase in IL-8, (3) an increase in IL-22, and (4) an increase or decrease in ferritin expression; and
   (iv) administering to the subject a therapeutically effective amount of an anti-inflammatory drug that is a statin.

2. The method of claim 1, wherein the subject is already infected with Severe Acute Respiratory Syndrome Coronavirus 2 (SARS-CoV-2) when the statin is administered.

3. The method of claim 1, wherein the subject is not experiencing COVID-19 symptoms, and the statin is administered to the subject to prevent the subject from developing severe COVID-19 symptoms.

4. A method for reducing risk of severe COVID-19 symptoms in a subject exposed to or infected with Severe Acute Respiratory Syndrome Coronavirus 2 (SARS-CoV-2), the method consisting of:
   (i) obtaining a whole blood sample from the subject;
   (ii) quantifying protein levels of at least three of interleukin 6 (IL-6), IL-8, IL-22, and ferritin in the whole blood sample or a serum sample separated therefrom by contacting total protein extracted from the whole blood sample or the serum sample with antibodies specific to IL-6, IL-8, IL-22, and ferritin under conditions suitable for detection of antibody binding to obtain an expression profile, wherein either the antibodies specific to IL-6, IL-8, IL-22, and ferritin or the total protein extracted from the whole blood sample or the serum sample are arrayed on a solid substrate or arrayed in a three-dimensional matrix;

(iii) determining that the subject compared to a healthy subject has at least three of (1) an increase in IL-6, (2) an increase in IL-8, (3) an increase in IL-22, and (4) an increase or decrease in ferritin expression; and (iv) administering to the subject a therapeutically effective amount of an anti-inflammatory drug that is a statin, whereby the risk of severe COVID-19 symptoms in the subject is reduced.

5. The method of claim 4, wherein the subject is already infected with Severe Acute Respiratory Syndrome Coronavirus 2 (SARS-CoV-2) when the statin is administered.

6. The method of claim 4, wherein the subject is not experiencing COVID-19 symptoms, and the statin is administered to the subject to reduce the risk of the subject developing severe COVID-19 symptoms.

* * * * *

UNITED STATES PATENT AND TRADEMARK OFFICE
CERTIFICATE OF CORRECTION

| | |
|---|---|
| PATENT NO. | : 11,768,206 B2 |
| APPLICATION NO. | : 16/913840 |
| DATED | : September 26, 2023 |
| INVENTOR(S) | : Henry Winchester |

It is certified that error appears in the above-identified patent and that said Letters Patent is hereby corrected as shown below:

In the Specification

Column 10, Line 58, "11-6, IL-8, and 11-22" should be --IL-6, IL-8, and IL-22--.

Signed and Sealed this
Fourteenth Day of May, 2024

Katherine Kelly Vidal
*Director of the United States Patent and Trademark Office*